United States Patent
Herzig

(10) Patent No.: US 8,722,926 B2
(45) Date of Patent: May 13, 2014

(54) BETA-KETOCARBONYLQUAT COMPOUNDS AND PROCESS FOR THE PREPARATION THEREOF

(75) Inventor: Christian Herzig, Waging (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/812,117

(22) PCT Filed: Jul. 20, 2011

(86) PCT No.: PCT/EP2011/062465
§ 371 (c)(1),
(2), (4) Date: Jan. 24, 2013

(87) PCT Pub. No.: WO2012/016837
PCT Pub. Date: Feb. 9, 2012

(65) Prior Publication Data
US 2013/0123535 A1    May 16, 2013

(30) Foreign Application Priority Data
Aug. 4, 2010 (DE) .......... 10 2010 038 887

(51) Int. Cl.
*C07C 59/245* (2006.01)
(52) U.S. Cl.
USPC .......................................... 562/77
(58) Field of Classification Search
USPC ........................................ 562/577
See application file for complete search history.

(56) References Cited

U.S. PATENT DOCUMENTS

| | | | |
|---|---|---|---|
| 5,028,236 | A | 7/1991 | Kortmann et al. |
| 5,942,588 | A | 8/1999 | Ettl et al. |
| 2003/0092804 | A1 | 5/2003 | Detering et al. |
| 2009/0247629 | A1 | 10/2009 | O'Lenick et al. |
| 2011/0024679 | A1 | 2/2011 | Herzig |

FOREIGN PATENT DOCUMENTS

| | | |
|---|---|---|
| CH | 388246 A | 9/1964 |
| EP | 1259672 B1 | 3/2007 |
| GB | 1000383 A | 8/1965 |
| WO | 96/26318 A1 | 8/1996 |
| WO | 2009/121751 A1 | 10/2009 |

OTHER PUBLICATIONS

Tidwell, 2006, Science of Synthesis, vol. 23, p. 391-492).*
Buchi J. et al., "Synthesis and Action of Several Curare-like Diammonium Derivatives With Ester, Ketone, and Alcohol Functions," Arzneimittel Forschung. Drug Research, ECV Editio Cantor Verlag, Aulendorf, DE, Bd. 10, No. 9, Jan. 1, 1960, pp. 699-709, XP008143988, ISSN: 0004-4172.

* cited by examiner

*Primary Examiner* — Rebecca Anderson
*Assistant Examiner* — Karen Cheng
(74) *Attorney, Agent, or Firm* — Brooks Kushman P.C.

(57) ABSTRACT

β-ketocarbonylquats contain at least one quaternary ammonium salt group, and may be prepared by the reaction of an alkyl ketene dimer with a tertiary amine group-containing compound also containing a protic group, followed by quaternization.

8 Claims, No Drawings

BETA-KETOCARBONYLQUAT COMPOUNDS AND PROCESS FOR THE PREPARATION THEREOF

CROSS-REFERENCE TO RELATED APPLICATIONS

This application is the U.S. national phase of PCT Application No. PCT/EP2011/062465 filed Jul. 20, 2011 which claims priority to German application 10 2010 038 887.4 filed Aug. 4, 2010, the disclosures of which are incorporated in their entirety by reference herein.

BACKGROUND OF THE INVENTION

1. Field of the Invention

The present invention relates to quats, i.e., compounds that contain at least one quaternary ammonium group, and processes for preparation thereof.

2. Description of the Related Art

EP 1 259 672 B1 describes the use of alkyl-ketene dimer dispersions for the crease-resist finishing of textiles. Also described are cationic emulsifiers prepared from alkyl-ketene dimer and polyethyleneimine in a partial reaction. Except for these partial-reaction products, in which some amine groups of the polyethyleneimine are amidated, the dispersed alkyl-ketene dimer remains intact and ends up as such on the fiber. Quaternization of the partially converted polyethyleneimine emulsifier is not described and would also be scarcely economical owing to the high percentage of primary and secondary amino groups.

Alkyl-ketene dimer dispersions useful as textile auxiliaries are described in the following documents: CH 388246 describes the use of formulations which contain the ketene softener "Aquapel" 380 (Hercules Powder Co.) for impregnating and hydrophobicizing textiles. U.S. Pat. No. 5,028,236 also utilizes alkyl-ketene dimers for hydrophobicizing wool and nylon fibers. The same purpose is behind the use of alkyl-ketene dimer dispersions in WO 96/26318 as sizing agents for paper, i.e., controlled hydrophobicization.

WO 2009/121751 describes the reaction of aminosiloxanes with alkyl-ketene dimers for preparing waxes of very high polydimethylsiloxane content. Quaternary compounds cannot be prepared in this way.

US 2009/247629 A1 describes the preparation of polymeric organic quats obtainable by esterifying a dimer acid with a dimethylaminoalkanol and then reacting with polyether epichlorohydrins. This sequence of syntheses is relatively involved and must be performed at high temperature (200° C.) over many hours (3-8 h), i.e., is somewhat unattractive.

The problem addressed by the present invention is that of providing quats (i.e., compounds containing at least one quaternary ammonium group) that can be prepared quickly and almost quantitatively in a simple process and have a comparatively long-chain hydrocarbon radical, preferably a fatty acid radical.

SUMMARY OF THE INVENTION

An object of the present invention is to provide a β-ketocarbonylquat containing one or more β-ketocarbonyl groups of the general formula $$R-CH_2-(C=O)-CHR-(C=O)- \quad (I)$$

also containing one or more quaternary ammonium groups, wherein

R is an aliphatic hydrocarbon radical of 6 to 28 carbon atoms, preferably 10 to 26 carbon atoms and more preferably 12 to 20 carbon atoms and may be the same or different in each occurrence, and to a process for preparing them. The process involves reacting an alkyl-ketene dimer with amino compounds containing at least one protic group to form compounds containing at least one tertiary amino group, and then quaternizing.

DETAILED DESCRIPTION OF THE PREFERRED EMBODIMENTS

Quaternary ammonium groups are derivatives of an ammonium group which have all four hydrogen atoms replaced by four N—C-bonded (optionally substituted) hydrocarbon groups, such as alkyl groups.

Preferably, the β-ketocarbonyl group of formula (I) is bonded to a radical Y, wherein Y is a divalent radical of the formula —O—, —NH—, —NR$^1$—, preferably —NH—, —NR$^1$—, or a trivalent radical of the formula =N—, and R$^1$ is a monovalent hydrocarbon radical of 1 to 30 carbon atoms, preferably 1 to 18 carbon atoms.

The β-ketocarbonylquats of the present invention preferably contain one or two quaternary nitrogen atoms, preferably one quaternary nitrogen atom. They have a molecular weight ($M_n$) of preferably at least 300 daltons and more preferably in the range from 500 to 2000 daltons. Charge density is preferably in the range from 0.5 to 2.0 mequiv. of N$^+$/g.

Preferred β-ketocarbonylquats are those of the general formula $$[R^3R^4R^5N^{(+)}-R^2-]_aY-ZX^{(-)} \quad (II)$$

wherein a is 1 or 2, with the proviso that when a=1, Y is a divalent radical and when a=2, Y is a trivalent radical, Y is a divalent radical of formula —O—, —NH—, —NR$^1$—, or a trivalent radical of formula =N—, X$^{(-)}$ is a counter-ion to the positive charge on the quaternary nitrogen atom, Z is a β-ketocarbonyl group of the formula $$R-CH_2-(C=O)-CHR-(C=O)- \quad (I)$$

R is as defined above,

R$^1$ is a monovalent hydrocarbon radical of 1 to 30 carbon atoms, preferably 1 to 18 carbon atoms, R$^2$ is a divalent $C_1$-$C_{18}$ hydrocarbon radical which may contain one or more separate oxygen atoms, R$^3$ is a monovalent hydrocarbon radical of 1 to 30 carbon atoms, preferably 1 to 18 carbon atoms, and is the same or different in each occurrence, R$^4$ is R$^3$ or a radical of the formula $$-R^1-Y-Z \text{ or } -R^1-N^{(+)}R^3{}_2R^5X^{(-)},$$

or R$^3$ and R$^4$ together or two R$^3$ radicals together are a divalent $C_3$-$C_{12}$ hydrocarbon radical which may optionally contain an oxygen atom or a nitrogen atom, and R$^5$ is a monovalent hydrocarbon radical of 1 to 18 carbon atoms, preferably 1 to 12 carbon atoms.

The present invention further provides a process for preparing the β-ketocarbonylquat, which process comprises a first step of reacting an alkyl-ketene dimer (1) of general formula

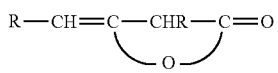 (III)

wherein R is as defined above, with amino compounds (2) which contain at least one tertiary amino group and at least one protic group selected from the group consisting of the formulae —OH, —$NH_2$, —$NHR^1$ and —NH—, preferably —$NH_2$, —$NHR^1$ and —NH—, wherein $R^1$ is as defined above, to obtain compounds (3) comprising tertiary amino groups, and a second step of partly or wholly quaternizing the tertiary nitrogen atoms from said compounds (3) obtained in the first step, with alkylating agents (4).

R is preferably an alkyl radical and more preferably a linear alkyl radical, of not less than 6 to 28 carbon atoms, preferably 10 to 26 carbon atoms and more preferably 12 to 20 carbon atoms.

$R^1$ is preferably an alkyl radical of 1 to 18 carbon atoms.

$R^3$ and $R^4$ are preferably alkyl radicals or cycloalkyl radicals. Preferably, at least one of $R^3$, $R^4$ and $R^5$ is a methyl or ethyl radical.

Examples of R radicals are alkyl radicals such as hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals, such as the cyclopentyl, cyclohexyl, cycloheptyl and methylcyclohexyl radicals; alkenyl radicals such as the vinyl, 5-hexenyl, cyclohexenyl, 1-propenyl, allyl, 3-butenyl and 4-pentenyl radicals; and alkynyl radicals such as the ethynyl, propargyl and 1-propynyl radicals.

Examples of $R^1$ hydrocarbon radicals are alkyl radicals such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals, such as the n-decyl radical, dodecyl radicals such as the n-dodecyl radical, and octadecyl radicals such as the n-octadecyl radical; cycloalkyl radicals such as cyclopentyl, cyclohexyl, cycloheptyl and methylcyclohexyl radicals; alkenyl radicals such as the vinyl, 5-hexenyl, cyclohexenyl, 1-propenyl, allyl, 3-butenyl and 4-pentenyl radicals; and alkynyl radicals such as the ethynyl, propargyl and 1-propynyl radical; aryl radicals such as the phenyl, naphthyl, anthryl and phenanthryl radicals; alkaryl radicals such as the o-, m- and p-tolyl radicals, xylyl radicals and ethylphenyl radicals; and aralkyl radicals such as the benzyl radical, and the α- and β-phenylethyl radicals.

Examples for $R^1$ hydrocarbon radicals fully hold for $R^3$ and $R^4$ hydrocarbon radicals.

Examples of $R^2$ divalent hydrocarbon radicals are alkylene radicals of the formulae

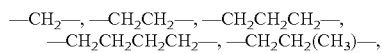

and examples of $R^2$ divalent hydrocarbon radicals which may contain one or more separate oxygen atoms are those of the formulae

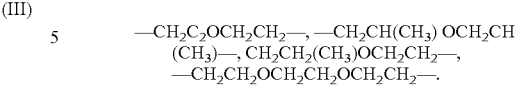

Examples of alkyl-ketene dimers (1) are those which derive from $C_8$ to $C_{30}$ carboxylic acids. The R hydrocarbon radicals may be linear, branched or cyclic, linear radicals being preferred. They can be saturated and also mono- or polyunsaturated, in which case saturated linear hydrocarbon radicals are preferred. Preferred alkyl-ketene dimers (1) derive from $C_{12}$ to $C_{28}$ carboxylic acids, and those based on $C_{14}$ to $C_{22}$ carboxylic acids are particularly preferred. The preparation of alkyl-ketene dimers (1) from carboxylic acids is described in U.S. Pat. No. 5,028,236. The general rule is that the number of carbon atoms in the R radical is equal to the number of carbon atoms in the carboxylic acids underlying the alkyl-ketene dimers (1) minus 2. In lieu of one alkyl-ketene dimer of defined chain length R there may also be used mixtures of various alkyl-ketene dimers (1), each differing in the length of R, as are obtainable for example from carboxylic acid mixtures originating in natural sources. Suitable fatty alkyldiketenes are described in EP 1 259 672 B1 at page 2 lines 52-57.

The amino compounds (2) used in the first step of the process according to the present invention contain at least one tertiary amino group and additionally also at least one protic group selected from the group consisting of the formulae —OH, —$NH_2$, —NHR and —NH—. This protic group serves to react with the alkyl-ketene dimer (1) in a first step and hence to bond in the first step at least one tertiary amino group to the alkyl-ketene dimer. The compound (3) obtained in the first step of the process according to the present invention thus contains at least one tertiary amino group. In the second step of the process according to the present invention, the tertiary amino groups thus bonded are partly or wholly quaternized with alkylating agents (4).

The first step of the process preferably utilizes amino compounds (2) of the general formula

 (IV)

wherein $R^{4'}$ is $R^3$ or a radical of the formula —$R^1$—Y—H or —$R^1$—$NR^3_2$, and a, $R^1$, $R^2$, $R^3$ and Y are each as defined above.

Examples of tertiary amino compounds (2) that additionally bear at least one further protic nitrogen function are:
3-dimethylaminopropylamine,
3-dimethylaminopropylbutylamine,
bis(3-dimethylaminopropyl)amine,
bis(3-aminopropyl)methylamine,
3-diethylaminopropyl-1-methylamine,
2-diethylaminoethylamine,
3-aminopropyl-3-dimethylaminopropylamine.

Examples of tertiary amino compounds (2) that additionally bear at least one further OH group are:
2-diethylaminoethanol,
2-dimethylaminoethanol,
3-dimethylaminopropanol,
2-dimethylamino-1-methylethanol,
bis(hydroxyethyl)methylamine,
2-cyclohexylaminoethanol,
2-morpholinoethanol,
2-(2-dimethylaminoethoxy)ethanol,
N,N,N-trimethyl-N-hydroxyethylbisaminoethyl ether, bis(3-dimethylaminopropyl)hydroxyethylamine,
3-dimethylaminopropyl-bis-(2-hydroxyethyl)amine,
3-dimethylaminopropyl-2-hydroxyethylamine,
tris(2-hydroxyethyl)amine.

Further examples of tertiary amino compounds (2) are the recited amino compounds in their ethoxylated or propoxylated form.

Suitable alkylating agents (4) for use in the second step of the process include any compound that has a quaternizing effect on tertiary amino groups.

Alkylating agents (4) preferably have the formula $$R^5\text{—}X \qquad (V)$$

wherein
R$^5$ is as defined above, and
X is a radical which in the step of alkylating the tertiary nitrogen atoms in said compounds (3) forms a counter-ion X$^-$ to the positive charge on the quaternary nitrogen atom.

R$^5$ is preferably a linear, branched or cyclic alkyl radical of 1 to 6 carbon atoms.

Examples of R$^5$ radicals are the methyl, ethyl, propyl, isopropyl, butyl, isobutyl and cyclohexyl radicals.

Examples of suitable alkylating agents (4) are dialkyl sulfates, such as dimethyl sulfate and diethyl sulfate, sulfonic esters, such as methyl p-toluenesulfonate, ethyl p-toluenesulfonate, propyl p-toluenesulfonate, and also benzyl compounds, such as benzyl chloride, benzyl bromide and benzyl iodide. Dimethyl sulfate, diethyl sulfate and methyl p-toluenesulfonate are particularly preferred.

Examples of counter-ions X$^-$ to the positive charge on the quaternary nitrogen atom are
$CH_3SO_4^-$
$CH_3CH_2SO_4^-$
$C_6H_5SO_3^-$
p-$CH_3(C_6H_4)SO_3^-$
$CH_3SO_3^-$
$C_4H_9SO_3^-$
$C_8H_{17}SO_3^-$
$Cl^-$, $Br^-$ and $I^-$.

The two-stage process of the present invention can be carried out in two separate steps of synthesis as well as preferably in a tandem process in one reaction system. Since the alkyl-ketene dimers (1) are mostly solid at 25° C., the first step of the process is preferably carried out at elevated temperature in the range from 40 to 140° C., preferably at 50 to 120° C. The second step of the process preferably takes place at 60 to 140° C. If desired, the entire synthesis is advantageously performable in one operation without cooling down in between.

The process of the present invention is preferably carried out at the pressure of the ambient atmosphere, i.e., at 1020 hPa for instance, but can also be carried out at higher or lower pressures.

The first step of the process according to the present invention utilizes alkyl-ketene dimer (1) in amounts of preferably 0.8 to 1.2 mol of diketene and preferably 0.9 to 1.1 mol of diketene per mole of protic group in amino compound (2).

It is particularly preferable to use alkyl-ketene dimers (1) in an equimolar amount relative to the protic groups in amino compounds (2). It must be borne in mind here that (1) is rarely pure alkyl-ketene dimer and is usually commercially available at a purity of 85 to 95%.

The second step of the process according to the present invention preferably utilizes alkylating agents (4) in amounts of 0.8 to 1.0 mol, preferably 0.9 to 1.0 mol, per mole of tertiary nitrogen atom in compound (3). The purity of the alkylating agent must be taken into account here as well as that of the other components. Should these contain impurities that likewise react with the alkylating agent, complete quaternization of tertiary nitrogen atoms may also require more than the preferred 1.0 mol of alkylating agent per mole of tertiary nitrogen atom.

The process of the present invention is advantageous over the process for preparing the familiar esterquats described in US 2009/0247629 A1, for example, in that the amidation in the first step of the process takes less than 30 minutes at 60° C. versus US 2009/0247629 A1 where the esterification, which moreover is never complete, takes many hours (3-8 hours) at 200° C. and the subsequent conversion of the ester amine to the esterquat takes a further 6-9 hours at 90° C.

A further advantage is that the present invention provides an almost quantitative quaternization, as compared with a 60-90% degree of quaternization in the prior art preparation of esterquats.

As a result, no excesses of alkylating agent (4) have to be used to achieve an almost quantitative quaternization and therefore there are no toxic alkylating agents (4) in the end product. Even when alkylating agent (4) is intentionally used in slight deficiency, the yields obtained are still very high. This provides for a very high active content and hence correspondingly minimized wastewater burden due to by-products.

A further advantage is that the β-ketocarbonylquats of the present invention are biodegradable.

The β-ketocarbonylquats of the present invention exhibit a surprisingly high hydrophilicity compared with the familiar esterquats, which are hydrophobic. The excellent hydrophilicity is also surprising because alkyl-ketene dimer dispersions have long been used worldwide for controlled hydrophobicization of paper (paper sizing), and comparable uses are known from CH 388246 and U.S. Pat. No. 5,028,236.

In their preferred amide form, the β-ketocarbonylquats of the present invention are also appreciably more stable to hydrolysis than the commercially available esterquats, which can therefore only be handled and used within a narrow pH range.

The process of the present invention can also be used to prepare bactericidal β-ketocarbonylquats having a longer alkyl chain R.

The supremely graduated reactivity of alkyl-ketene dimer also makes it possible to use amino compound (2) with OH groups, such as dimethylaminoethanol, to prepare corresponding alkyl-ketene dimer esterquats when ester groups are desired between the hydrophobic portion and the hydrophilic portion.

The β-ketoamide structure in the βketocarbonylquats of the present invention has the advantage that it can be used for complexation of metal ions. This provides further possible means of attachment to surfaces.

Example 1

119 g of alkyl-ketene dimer having a diketene equivalent weight of 570 g/mol (alkyl radical R about 16 carbon atoms, commercially available as "AKD" from Trigon Chemie GmbH) are carefully melted without overheating. At 63° C., 21.4 g of 3-dimethylaminopropylamine are gradually metered in with cooling and efficient stirring, so an internal temperature of 75° C. is not exceeded. A few minutes after completion of the metered addition the amidation has concluded. An amidoamine is obtained with an amine number of 1.48 (theoretically 1.49), indicating a virtually 100% yield.

The amidoamine obtained is heated to 100° C. and altogether 37.2 g of methyl p-toluenesulfonate (0.95 mol per mole of tertiary amino group in the amidoamine) are added over a period of 30 minutes. The system is allowed to react at 100° C. for a further 2 hours to obtain 177.6 g of a dialkylacetoacetamidoquat, which solidifies on cooling. The product has an amine number of 0.07, which corresponds to a quaternization of about 94%. This value is in good agreement with the intended 5% underfeeding of the methyl p-toluenesulfonate (MeOTs).

Example 2

119 g of the alkyl-ketene dimer described in Example 1 (570 g/mol of diketene) are gradually admixed at 61° C. with altogether 39.2 g of bis(3-dimethylaminopropyl)-amine (commercially available under the tradename "JEFFCAT Z 130" from Huntsman). The exothermic amidation reaction concludes shortly after terminating the end of the metered addition. Thereafter, the amidoamine obtained is admixed at 100° C. with 74.5 g of methyl p-toluenesulfonate (0.95 mol per mole of tertiary amino group in the amidoamine) added a little at a time, while the reaction mixture reaches 118° C. The reaction is allowed to go to completion at 100° C. in the course of 2 hours. According to an amine number of 0.11, about 94% of the tertiary amino groups have been quaternized.

Example 3

Example 1 is repeated except that the amount of alkylating agent is raised to 100% (39.0 g) and hence is made equimolar to the amount of tertiary amine. This gives 179.4 g of the same dialkylacetoacetamidoquat as in Example 1, but with an amine number of just 0.02, which corresponds to a degree of quaternization equal to 98%.

Example 4

At 65° C., 119 g of the molten alkyl-ketene dimer described in Example 1 (570 g/mol diketene) are reacted with 18.6 g of 2-dimethylaminoethanol, which is added over a period of 12 minutes. The immediately ensuing exothermic reaction causes the mixture to heat up by 6° C. despite cooling. After one hour at 100° C., 37 g of methyl p-toluenesulfonate are metered into the alkyl-ketene dimer aminoester and the reaction mixture is allowed to react for a further 2 hours, which is accompanied by a distinct increase in viscosity. 174.6 g are obtained of an esterquat which solidifies on cooling and has an amine number of 0.07 and completely converted alkylating agent (methyl p-toluenesulfonate). This corresponds to a quaternization of around 94%, corresponding to the 5% underfeed for methyl p-toluenesulfonate (MeOTs).

As the examples show, the process of the present invention provides esterquats as well as amidoquats rapidly and in very high yields. Similarly, the degree of quaternization is efficiently controllable and can be driven to quantitative conversions.

The invention claimed is:

1. A β-ketocarbonylquat having the formula $$[R^3R^4R^5N^{(+)}-R^2-]_aY-ZX^{(-)} \quad (II)$$

wherein
a is 1 or 2, with the proviso that when
a is 1, Y is a divalent radical and
when a is 2, Y is a trivalent radical,
Y is a divalent radical of formula —O—, —NH—, —NR$^1$—, or a trivalent radical of formula =N—,
$X^{(-)}$ is a counter-ion to the positive charge on the quaternary nitrogen atom,
Z is a β-ketocarbonyl group of the formula $$R-CH_2-(C=O)-CHR-(C=O)- \quad (I)$$

R each, independently is an aliphatic hydrocarbon radical of 6 to 28 carbon atoms,
$R^1$ is a monovalent hydrocarbon radical of 1 to 30 carbon atoms,
$R^2$ is a divalent $C_1$-$C_{18}$ hydrocarbon radical which optionally contain one or more separate oxygen atoms,
$R^3$ each, independently, is a monovalent hydrocarbon radical of 1 to 30 carbon atoms,
$R^4$ is $R^3$ or a radical of the formula $$-R^1-Y-Z \text{ or } -R^1-N^{(+)}R^3{}_2R^5X^{(-)},$$

or $R^3$ and $R^4$ together or two $R^3$ radicals together are a divalent $C_3$-$C_{12}$ hydrocarbon radical which optionally contains an oxygen atom or a nitrogen atom, and
$R^5$ is a monovalent hydrocarbon radical of 1 to 18 carbon atoms.

2. The β-ketocarbonylquat of claim 1, wherein the aliphatic hydrocarbon radical R contains 10-26 carbon atoms.

3. The β-ketocarbonylquat of claim 1, wherein the aliphatic hydrocarbon radical R contains 12-20 carbon atoms.

4. The β-ketocarbonylquat of claim 1, wherein Y is —NH—, —NR$^1$—, or a trivalent radical of the formula =N—.

5. The β-ketocarbonylquat of claim 1, wherein $R^1$ contains 1-18 carbon atoms.

6. A process for preparing a β-ketocarbonylquat of claim 1, comprising:
in a first step,
reacting an alkyl-ketene dimer of the formula

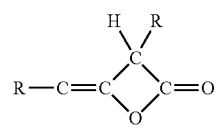

(III)

wherein R each, independently, is an aliphatic hydrocarbon radical of 6 to 28 carbon atoms,
with at least one amino compound of the formula IV which contains at least one tertiary amino group and at least one protic group selected from the group consisting of the formulae —OH, —NH$_2$, —NHR$^1$ and —NH—, and mixtures thereof, wherein $R^1$ is a monovalent hydrocarbon radical of 1 to 30 carbon atoms,
to obtain compounds comprising tertiary amino groups,
and in a second step, partly or wholly quaternizing the tertiary nitrogen atoms from said compounds comprising tertiary amino groups obtained in the first step, with an alkylating agent to form a β-ketocarbonylquat of the formula II, wherein amino compound(s) of the formula IV have the formula $$[R^3R^4N-R^2-]_aY-H \quad (IV)$$

wherein
$R^{4'}$ is $R^3$ or a radical of the formula —R$^1$—Y—H or —R$^1$—NR$^3{}_7$; and
a is 1 or 2, with the proviso that when
a is 1, Y is a divalent radical and
when a is 2, Y is a trivalent radical,
$R^1$ is a monovalent hydrocarbon radical of 1 to 30 carbon atoms, $R^2$ is a divalent $C_1$-$C_{18}$ hydrocarbon radical which optionally contain one or more separate oxygen atoms, $R^3$ each, independently, is a monovalent hydrocarbon radical of 1 to 30 carbon atoms, and Y is a divalent radical of formula —O—, —NH—, $NR^1$—, or a trivalent radical of formula =N—.

7. The process of claim 6, wherein an alkylating agent used in the second step of the process has the formula $$R^5\text{—}X \tag{V}$$

wherein $R^5$ is a monovalent hydrocarbon radical of 1 to 18 carbon atoms,

X is a radical which forms a counter-ion $X^-$ to the positive charge on the quaternary nitrogen atom.

8. The process of claim 6, wherein an alkylating agent in the second step of the process are dialkyl sulfates, sulfonic esters, or mixtures thereof.

* * * * *